United States Patent [19]

Malcher et al.

[11] Patent Number: 5,595,175

[45] Date of Patent: Jan. 21, 1997

[54] INHALER FOR ADMINISTRATION OF POWDERY SUBSTANCES

[75] Inventors: Eric Malcher, St. Louis, France; Kurt Zechner, Allschwil, Switzerland

[73] Assignee: Sandoz Ltd., Basel, Switzerland

[21] Appl. No.: 218,551

[22] Filed: Mar. 28, 1994

Related U.S. Application Data

[63] Continuation of Ser. No. 930,862, Aug. 14, 1992, abandoned.

[30] Foreign Application Priority Data

Aug. 16, 1991 [DE] Germany ............................ 41 27 097.5

[51] Int. Cl.⁶ .......................... A61M 15/00; A61M 16/00; B05D 7/14; B65D 83/06
[52] U.S. Cl. .................. 128/203.15; 128/203.21
[58] Field of Search ......................... 128/203.15, 203.21; 604/54; 221/69, 72, 82, 85, 81, 76, 77; 206/528–540; 220/506

[56] References Cited

U.S. PATENT DOCUMENTS

| | | | |
|---|---|---|---|
| 4,274,550 | 6/1981 | Feldstein | 221/71 |
| 4,860,740 | 8/1989 | Kirk et al. | 128/203.15 |
| 4,889,114 | 12/1989 | Kladders | 128/203.15 |
| 5,207,217 | 5/1993 | Cocozza et al. | 128/203.21 |

FOREIGN PATENT DOCUMENTS

| | | | |
|---|---|---|---|
| 0406893 | 1/1991 | European Pat. Off. | 128/203.15 |
| 906485 | 12/1990 | South Africa | 128/203.15 |
| 2142246 | 1/1985 | United Kingdom | 128/203.15 |

*Primary Examiner*—Kimberly L. Asher
*Attorney, Agent, or Firm*—Robert S. Honor; Melvyn M. Kassenoff; John L. Chiatalas

[57] ABSTRACT

An inhaler for administering powdered medicaments comprising a one-piece, elongate body that has an elongate magazine in a magazine passage extending through the elongate body. The elongate body also has an air inlet, a mouthpiece, and a capsule cutter. The elongate magazine has a plurality of capsule chambers defined in it and spaced along its length, each capsule chamber having an air inlet alignable with the air inlet to the elongate body and an air outlet alignable with the mouthpiece. The magazine is slidable step-wise along the magazine passage to align a capsule chamber with the air inlet to the elongate body, the mouthpiece and the capsule cutter. The capsule cutter, upon activation, pierces both ends of a capsule in the capsule chamber.

11 Claims, 3 Drawing Sheets

INHALER FOR ADMINISTRATION OF POWDERY SUBSTANCES

This is a continuation of application Ser. No. 07/930,862, filed Aug. 14, 1992, now abandoned.

This invention relates to an inhaler suitable for use in the administration of powdered medicaments contained in a capsule.

Inhalation is a very convenient way of administering a large number of medicaments. Many types of inhalers are known but the present trend is towards inhalers which do not require pumps or propellants to deliver the medicament. Instead, many inhalers are now designed so that inhalation itself causes sufficient entrainment of the medicament in the inhaled air stream.

European patent publication 0 147 755 discloses one example of such an inhaler. The inhaler consists of a two-piece housing that is substantially cylindrical in shape. The two pieces are movable relative each other along the axis of the housing but are biased away from each other. A capsule chamber is defined in the housing to receive a capsule in use. An air inlet is connected to one end of the capsule chamber and an air outlet is connected to the opposite end of the capsule chamber and terminates in a mouthpiece. A pair of cutting blades, which are activated by depressing a button, are mounted in the housing to be movable into the capsule chamber to pierce both ends of the capsule in the chamber. However, the blades can only move into the capsule chamber once the two pieces have been pushed together against the bias. Once the button has been depressed and the capsule cut, the user inhales through the mouthpiece. Air is drawn into the capsule chamber through the air inlet, entrains the powdered medicament, and is inhaled by the user.

Disadvantages of this apparatus are that it is of complicated construction and difficult to use. Children and people with impaired co-ordination find it difficult to use because the two pieces must be pushed together and, simultaneously, the button must be depressed. Also to load the inhaler, the two pieces must be completely separated to gain access to the capsule chamber. This is inconvenient, time consuming and can result in exposure of the blades, which would be dangerous. Another disadvantage is that the inhaler must be reloaded after each use.

German patent publication DE 39 27 170 A1 discloses another example of such an inhaler. This inhaler consists of a housing, a revolver mechanism rotatably mounted in the housing, and a mouthpiece pivotally attached to the housing above the revolver mechanism. The revolver mechanism has six capsule chambers defined in it, of which one is positionable over the axis of the housing. In this position, the capsule chamber is connected to an air inlet at one end and an air outlet in the mouthpiece at its opposite end. A pair of blades are movably mounted in the housing to be movable into the capsule chamber over the axis upon depression of a button.

In use, the revolver mechanism is rotated until a capsule chamber aligns with the axis of the housing. The button is then depressed to cut the capsule in the housing. The user then inhales to draw air into the capsule chamber and entrain the medicament. To use the apparatus again, the user rotates the revolver mechanism until another capsule chamber containing a capsule aligns with the axis of the housing. Once all the capsules have been used, the mouthpiece is pivoted away from the housing to expose the revolver mechanism. The used capsules are then removed and replacement capsules are inserted.

One disadvantage of this apparatus is its complexity; there are many moving parts. Consequently the apparatus is expensive and is not meant to be disposed of after a short period of use. However the inhaler does have a finite working life after which it is likely not to operate satisfactorily. This can cause problems because users will often continue to use the inhaler to avoid the cost of replacing it. The inhaler is also difficult to clean.

It is an object of this invention to provide an inhaler that is simple in construction and hence inexpensive, easy to use, and is conveniently fed capsules from a magazine.

Accordingly, this invention provides an inhaler suitable for administering powdered medicaments. The inhaler comprises:

an elongate body having a magazine passage extending through it from one end to the other, an air inlet to the passage, an air outlet from the passage on the opposite side of the passage that terminates in a mouthpiece, and a capsule cutting means aligned between the air inlet and the air outlet; and an elongate magazine having a plurality of capsule chambers defined in it and spaced along its length, each capsule chamber having an air inlet alignable with the air inlet of the elongate body and an air outlet alignable with the air outlet of the elongate body, the magazine being slidable step-wise in and along the magazine passage to align a capsule chamber with the air inlet of the elongate body, the air outlet of the elongate body and the capsule cutting means; the capsule cutting means, upon activation, piercing both ends of a capsule in the capsule chamber to permit air flow through the capsule to release the medicament in the capsule.

Preferably, the inhaler further comprises a catch means co-operating between the elongate body and the magazine to releasably hold the magazine in aligned position in the elongate body. The catch means may comprise a plurality of resilient arms, each resilient arm extending in a recess in the magazine with a resilient arm positioned beneath each capsule chamber and each resilient arm having a tab at its distal end that projects outwardly of the magazine; the tab of the capsule chamber that is aligned with the capsule cutting means engaging with the elongate body to releasably secure the magazine in position.

Preferably, the tab engages in the air inlet of the elongate body when the magazine is secured in position. The body may be provided with a catch release means to disengage the tab from the air inlet. This catch release means may be in the form of a resilient body arm extending from the elongate body and having a ridge; the resilient body arm being movable inwardly to cause the ridge to push the resilient arm of the magazine inwardly to disengage the tab.

The magazine passage may be in the form of a channel extending across one side of the elongate body, the channel having a pair of opposing lips to hold the magazine in the channel. A perforated member may be positioned in the air outlet from the passage; the perforations in the perforated member being large enough to permit the flow of air and entrained medicament particles through it but small enough to prevent the flow of a capsule through it. The perforations may have a diameter of about 1 mm.

Preferably the capsule chambers are substantially cylindrical, the diameter of the cylinder being larger than the diameter of the capsule in the capsule chamber to permit the capsule to vibrate when air is drawn through the capsule chamber. Each capsule chamber may contain a holding means to hold the capsule steady during cutting.

The invention therefore provides an inhaler of simple construction in that it has a one piece housing and a simple, sliding magazine. Therefore the inhaler is relatively easy to manufacture and complicated moulding processes are not required. Also, despite its simplicity, the inhaler carries a plurality of capsules which makes it more convenient to use than inhalers which must be reloaded after each use. Further, the user need only slide the magazine into position and then activate the cutting means; complicated operational procedures are not required. Also, disassembly for reloading purposes is not required.

The invention also provides a disposable medicament kit comprising the inhaler described above together with a supply of capsules that contain an inhalable medicament in powdered form.

The capsules may be conveniently held in a blister pack. Preferably, sufficient capsules are provided for a month's usage. At the end of the month, the inhaler may be disposed of and a new kit purchased. In this way, the user will have a fully functional inhaler and will not be using an old inhaler which may not be functioning properly.

An embodiment of the invention is now described, by way of example only, with reference to the drawings in which.

Figure 5:
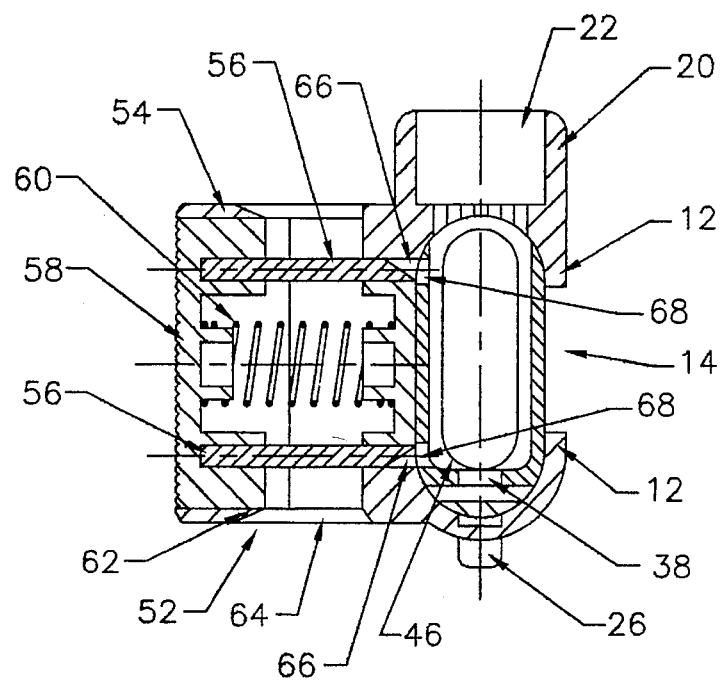
FIG. 5 is a cross sectional view taken along line CC in FIG. 2.

The inhaler 2 illustrated in the drawings comprises an elongated body 4 that has a channel 6 formed in one of its sides, the channel 6 extending along the length of the body 4 from a feed end 8 to the opposite, discharge end 10. The channel 6 is substantially oval in cross-section (as is best illustrated in FIG. 5). A pair of inwardly projecting lips 12 extend along the length of the channel 6, one on each side of the channel opening 14.

An air inlet 16, leading into the channel 6, is defined in an inlet edge 18 of the body 4 adjacent the discharge end 10 of the body 4. A mouthpiece 20 projects from the opposite, outlet edge 22 of the body 4, directly opposite the air inlet 16. The mouthpiece 20 has an air passage 22 extending through it that connects it to the channel 6. A perforated member 24 extends over the inlet to the air passage 22 in the channel 6. The size of the perforations in the perforated member 24 is chosen so that air and entrained medicament particles may pass freely through the perforated member 24 but any capsule (or portion of the capsule) containing the medicament may not.

Figure 6:
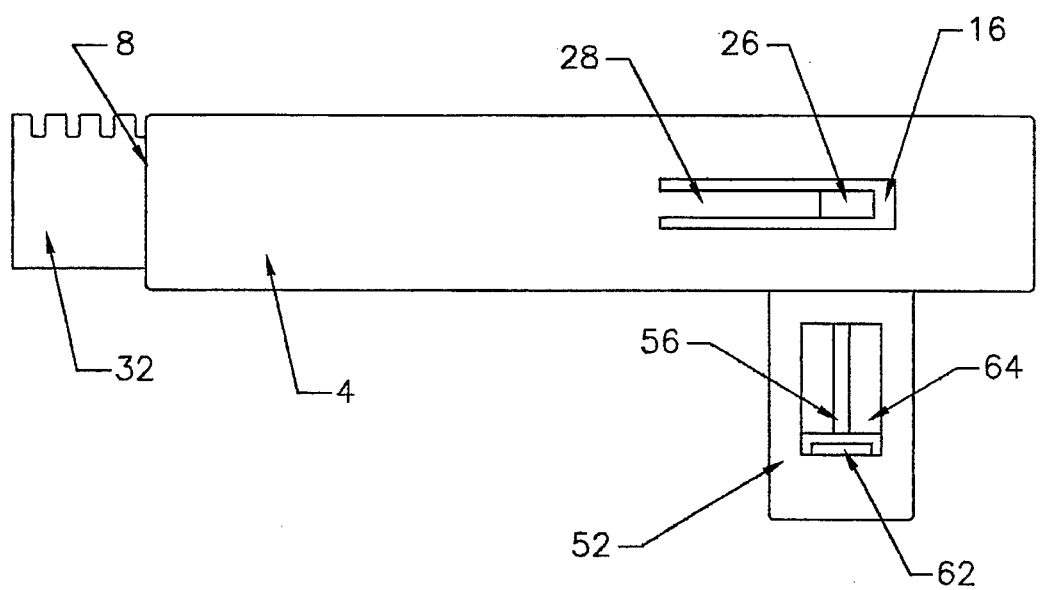
FIG. 6 is a bottom view of the inhaler.

A catch release 26 extends into the air inlet 16 on a resilient body arm 28. A ridge 30 of the catch release 26 projects into the channel 6. The catch release 26 is movable outwardly of the channel 6 so that no portion of it extends into the channel 6 but is biased by the resilient body arm 28 such that the ridge normally projects into the channel 6. The catch release 26 is also movable inwardly so that the ridge 30 projects further into the channel 6. As illustrated in FIG. 6, the catch release 26 does not block the air inlet 16.

Figure 1:
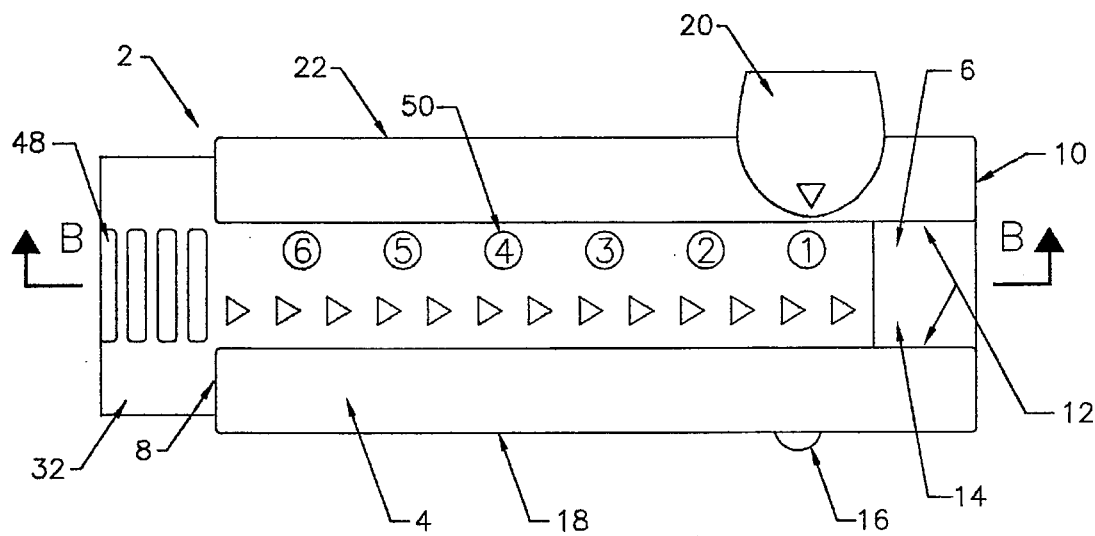
FIG. 1 is a side view of the inhaler.
Figure 2:
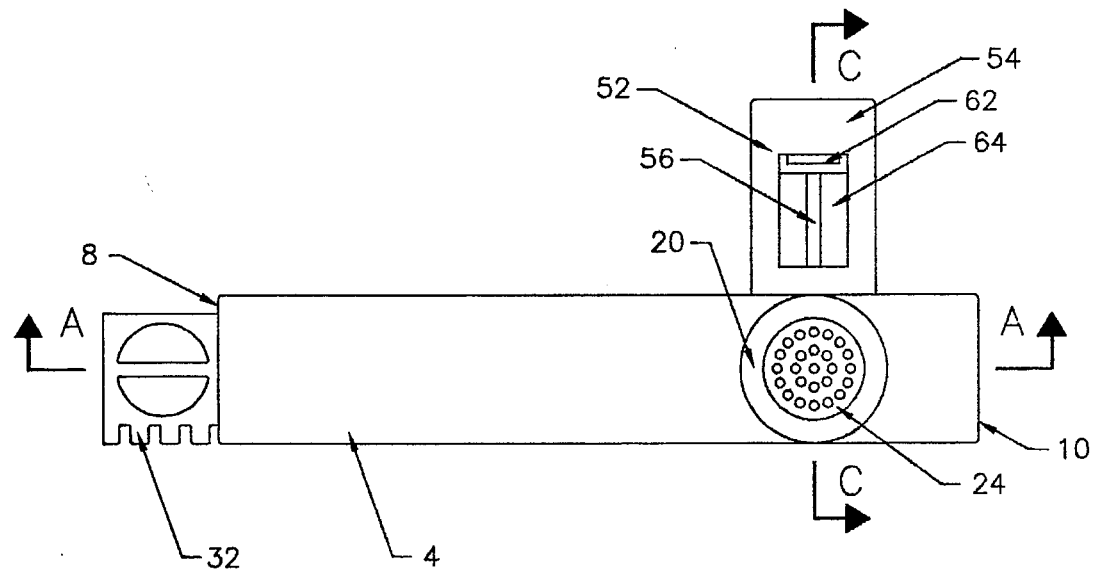
FIG. 2 is a top view of the inhaler.
Figure 3:
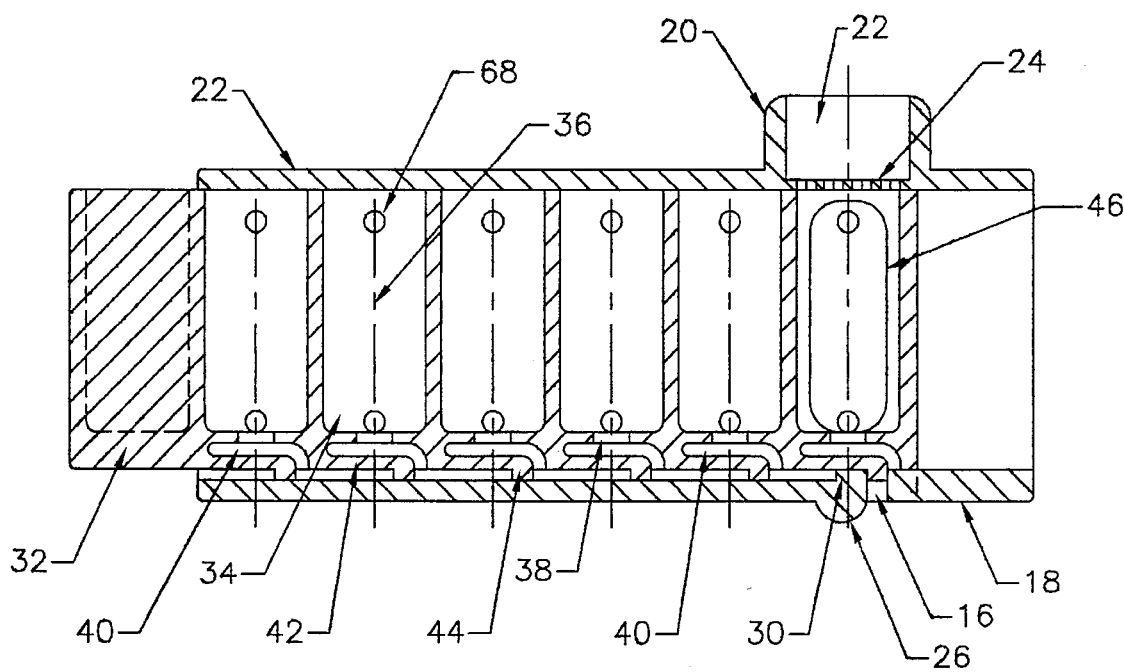
FIG. 3 is a cross sectional view taken along line AA of FIG. 2.
Figure 4:
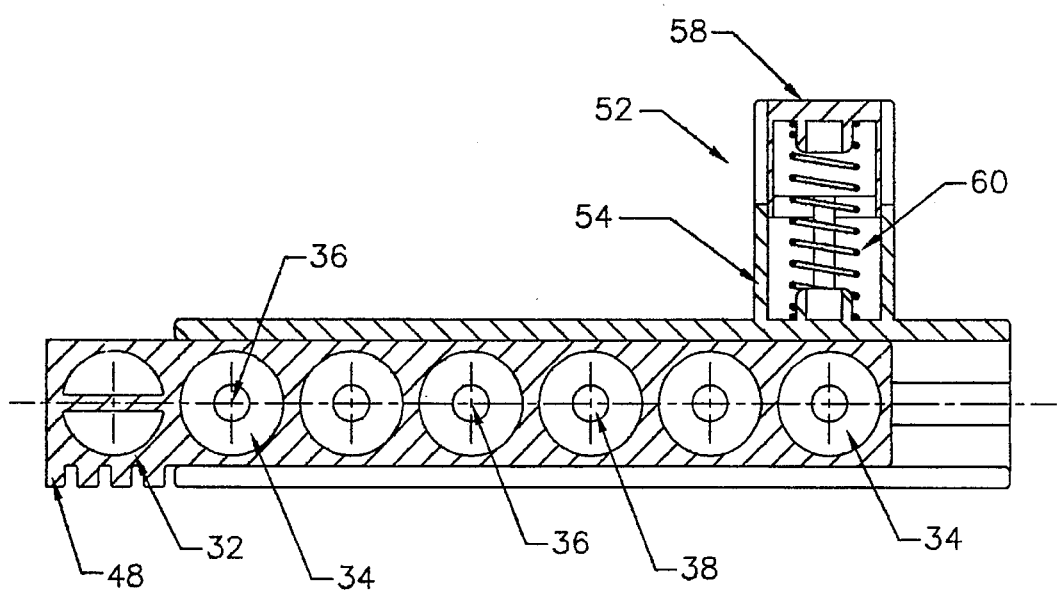
FIG. 4 is a cross sectional view taken along line BB in FIG. 1.

A capsule magazine 32 is pushed into the channel 6 at the feed end 8 and may be slid along the channel 6. The inwardly extending lips 12 hold the magazine 32 in the channel 6. The magazine 32 is elongate, substantially oval in cross-section, and has a plurality of chambers 34 defined in it; one after the other along its length. Each chamber 34 is substantially cylindrical in shape with the axis 36 of the cylinder aligned at right angles to the longitudinal axis of the magazine 32. An air inlet 38 extends into each chamber 34 at one end while the opposite end of the chamber 34 is open and forms an air outlet. A recess 40 is formed into the magazine 32 beneath each air inlet 38 and a resilient magazine arm 42 extends across each recess 40. A tab 44 projects outwardly a small distance from the distal end of the resilient magazine arm 42. As best illustrated in FIG. 3, in use the tab 44 engages around the catch release 26 of the body 4 and into the air inlet 16 to lock the magazine 32 in position. The magazine 32 is shown to have six capsule chambers 34 but this can be altered as desired. The magazine 32 is sized such that it is snugly received in the channel 6 but can be readily slid in the channel 6.

In use, a capsule 46 is positioned in each capsule chamber 34. The capsules 46 are each elongate cylinders that have rounded ends and are each arranged in a chamber 34 with the axis of the capsule 46 aligned substantially with the axis 36 of the chamber 34. In this way, one rounded end of each capsule 46 is adjacent the air inlet 38 of its chamber 34 and the opposite end is adjacent the open end of the chamber 34.

The magazine 32 has a plurality of ridges 48 at its trailing edge to provide better grip for the user. The magazine 32 also has a plurality of numbers 50 marked on it, each number 50 corresponding in position to a chamber 34 in the magazine 32. In this way, the user can readily determine how many capsules 46 are left in the magazine 32.

A cutting mechanism 52 extends from the body 4 on the side of the body 4 opposite to the channel opening 14. The cutting mechanism 52 is positioned such that it is in register with the mouthpiece 20 and the air inlet 16. The cutting mechanism 52 comprises a housing 54 projecting at right angles from the body 4 and a pair of blades 56 in the housing 54 connected at one end to a button 58. The blades 56 are spaced from each other a distance slightly less than the length of the capsule 46. The button 58 is movable, against the bias of a spring 60, into the housing 54. The button is prevented from leaving the housing 54 by a pair of laterally extending tabs 62 that each engage into a slot 64 in the side of the housing 54. However, any conventional cutting mechanism, such as that described in DE 39 27 170 A1, may be used.

A pair of blade passages 66 extend through the body 4, beneath the housing 54, into the channel 6 of the body 4. The blade passages 66 are spaced from each other the same distance as the spacing between the blades 56. The outlet of one blade passage 66 is positioned adjacent the air inlet 38 of the magazine 32 and the outlet of the other blade passage 66 is positioned adjacent the opposite end of the channel 6. A blade 56 is slidingly received in each blade passage 66. Depression of the button 58 therefore causes the blades 56 to slide in the blade passages 66 and into the channel 6 to pierce or cut the ends of a capsule 46 in the channel 6.

The magazine 32 also has a pair of blade passages 68 though one of its walls at each chamber 34. When the magazine 32 is correctly positioned in the channel 6, the blade passages 68 align with the blade passages 66 in the body 4.

The diameter of each chamber 34 is slightly larger than the diameter of the capsule 46 that is placed in it. A clearance of about 1 mm is preferred. In this way, when air is drawn through the chamber 34, the capsule 46 vibrates in the chamber 34. This ensures that very little of the medicament remains clogged in the capsule 46. Pins or ribs may be provided in each chamber 34 to hold the capsule 46 steady during cutting. Alternatively, a shallow, elongate recess may be formed into the wall of the chamber 34 into which the capsule is pushed by the blades 56 prior to cutting. Once in the recess, the capsules are less likely to move during cutting. Holding of the capsule in this way improves cutting consistency.

In use, a magazine 32 containing a capsule 46 in each chamber 34 is pushed into the channel 6 of a body 4. The magazine 32 is then slid along the channel 6 until the leading edge of the magazine 32 engages the ridge 30 of the catch release 26. The leading edge then rides over the ridge 30 by pushing the catch release 26, against the bias of the resilient body arm 28, out of the body 4. Further movement of the magazine 32 into the channel 6 causes the ridge 30 of the catch release 26 to ride over the tab 44 of the resilient magazine arm 42 until the resilient body arm 28 causes the ridge 30 to engage behind the tab 44. The bias of the resilient magazine arm 42 causes the tab 44 to engage in the air inlet 16. In this way, the leading chamber 34 is correctly aligned with the blades 56, the air inlet 16 and the mouthpiece 20 and is held in this position. The user then depresses the button 58 to cause the blades 56 to extend into the chamber 34. One blade 56 cuts one end of the capsule 46 in the chamber 34 and the other blade 56 cuts the other end of the capsule 46. The user then inhales through the mouth and air flows into the air inlet 16 and into the chamber 34 through the air inlet 38. The powdered medicament contained in the capsule 46 is entrained by the air and is carried through the perforated member 24 and through the mouthpiece 20 into the user's mouth and lungs.

The next time the user wishes to use the inhaler 2, the catch release 26 is pushed into the body 4. This causes the ridge 30 to push the resilient magazine arm 42 into the recess 40. This movement of the resilient magazine arm 42 draws the tab 44 out of the air inlet 16 and frees the magazine 32. The magazine 32 is then pushed further into the channel 6 until the next tab end 44 engages in the air inlet 16 and locks. The process then may be repeated as necessary. Once all the capsules 46 have been used, the used capsules 46 are disposed of and a new capsule 46 is inserted into each chamber 34. The magazine 32 is then reloaded in the channel 6.

Conveniently, the capsules 46 are contained in a blister pack and the user simply pops a capsule 46 from the blister pack into the empty chamber 34. The blister pack may be provided with a month's supply of capsules. The inhaler 2 is preferably packaged together with a blister pack (or packs) containing a month's supply of capsules. Therefore the user obtains a new inhaler 2 with each repeat dosage. The advantage of this is that the user will have an inhaler 2 in full working order and will not be attempting to use an old, inoperative inhaler. Since the inhaler 2 is simple and inexpensive, the cost of purchasing an inhaler 2 once a month will not be prohibitive.

The body 4 may be made of any suitable material but thermoplastics are preferred because they are inexpensive, light and mechanically sound. Polystyrene is a preferred thermoplastics material. The magazine 32 is also preferably made of thermoplastics.

The lips 12 of the channel 6 are spaced from one another a distance such that the channel opening 14 is smaller than the size of a small finger. In this way, the chances of inadvertent cutting of fingers on the blades 56 is reduced.

It will be appreciated that numerous modifications and variations may be made to the embodiment described without departing from the scope of the invention. For example, it is not necessary for the magazine 32 to slide in a channel 6 in the body 4; instead a totally enclosed passage through the body 4 may be used. Also, the air passage 22 in the mouthpiece 20 need not be sealed by the perforated member 22; instead, each of the chambers 34 may be sealed by a perforated sheet. Further, the capsules need not be fed into the capsule chambers 34 through an upper opening; instead feed slots may be provided in the sides of the magazine 32. The outlet of the capsule chamber 34 may then be smaller than the capsule, or may be a perforated member, to prevent the capsule from being drawn out of the chamber 32. The air inlet 16 also may be connectable to a pump means, for example a bellows. In this way air can be pumped through the chamber 34 rather than be drawn through it.

What is claimed is:

1. An inhaler for administering powdered medicaments comprising an elongate body having a first end, a second end, a magazine passage extending through the elongate body from the first end to the second end, an air inlet to the magazine passage, an air outlet from the magazine passage aligned opposite the air inlet and terminating in a mouthpiece, and a capsule cutter having blades and a blade actuator;

an elongate magazine releasably and slidably held in the magazine passage, the elongate magazine having a plurality of discrete, elongate capsule chambers defined in the elongate magazine and spaced along the length of the elongate magazine with the longitudinal axis of each capsule chamber arranged transverse to the longitudinal axis of the elongate magazine, each capsule chamber having an air inlet alignable with the air inlet of the elongate body, an air outlet alignable with the air outlet of the elongate body and blade ports to provide access for the blades into the capsule chamber, the magazine being slidable in and along the magazine passage; and a catch means co-operating between the elongate body and the elongate magazine for releasably holding the elongate magazine in one of a plurality of aligned positions in the elongate body in which, in each aligned position, a capsule chamber is aligned with the air inlet of the elongate body, the air outlet of the elongate body and the capsule cutter, an air flow passage being provided from the air inlet of the elongate body, through the capsule chamber and out of the mouthpiece, the elongate magazine being slidable in the magazine passage of the elongate body from one aligned position to the next; and in which the blades of the capsule cutter pierce both end of a capsule in the capsule chamber and the actuator causes the blades to enter the capsule chamber and pierce the capsule.

2. An inhaler according to claim 1 in which the catch means comprises a plurality of resilient arms, each resilient arm extending in a recess in the elongate magazine with a resilient arm positioned beneath each capsule chamber and each resilient arm having a tab at the distal end of said resilient arm that projects outwardly of the elongate magazine; the tab beneath the capsule chamber that is aligned with the capsule cutting means engaging with the elongate body to releasably secure the elongate magazine in position.

3. An inhaler according to claim 2 in which the tab engages in the air inlet of the elongate body to releasably secure the elongate magazine in position.

4. An inhaler according to claim 3 in which the elongate body has a catch release means to disengage the tab from the air inlet; the catch release means comprising a resilient body arm extending from the elongate body and having a ridge; the resilient body arm being movable inwardly for causing the ridge to push the resilient arm of the magazine inwardly for disengaging the tab from the air inlet.

5. An inhaler according to claim 1 in which the magazine passage is in the form of a channel extending across one side of the elongate body, the channel having a pair of opposing lips to hold the magazine in the channel.

6. An inhaler according to claim 1 in which a perforated member is positioned in the air outlet from the passage; the perforations in the perforated member being large enough to permit the flow of air and entrained medicament particles through said perforated member, but small enough to prevent the flow of a capsule or capsule fragments through said perforated member.

7. An inhaler according to claim 1 in which the capsule chambers are substantially cylindrical, the diameter of the cylinder being larger than the diameter of the capsule in the capsule chamber to permit the capsule to vibrate when air is drawn through the capsule chamber.

8. An inhaler according to claim 1 in which each capsule chamber contains a holding means for holding the capsule steady during cutting.

9. A disposable medicament kit comprising an inhaler according to claim 1 together with a supply of capsules that contain an inhalable medicament in powdered form.

10. A kit according to claim 9 in which the capsules are held in a blister pack.

11. In an inhaler for administering powdered medicaments that comprises an elongate body having a first longitudinal end, a second longitudinal end and a housing for a magazine, an air inlet to the housing, an air outlet from the housing aligned opposite the air inlet and terminating in a mouthpiece, and a capsule cutting means for piercing the ends of a capsule in the inhaler and aligned between the air inlet and air outlet, a magazine having a plurality of capsule chambers in the magazine and being releasably held in the housing, the improvement comprising said housing being in the form of an elongate passage that extends through the elongate body from the first longitudinal end to the second longitudinal end; and the magazine being in the form of an elongate magazine having the capsule chambers spaced along the length of the elongate magazine, each capsule chamber being elongate and arranged transverse to the longitudinal axis of the elongate magazine and having an air inlet alignable with the air inlet of the elongate body, an air outlet alignable with the air outlet of the elongate body, the elongate magazine being slidable in and along the elongate passage from one of a plurality of defined positions to the next, in which, in each defined position, a capsule chamber is aligned with the air inlet of the elongate body, the air outlet of the elongate body and the capsule cutting means, an air flow passage being provided from the air inlet of the elongate body, through the capsule chamber and out of the mouthpiece.

* * * * *